United States Patent [19]
Westlake, III et al.

[11] Patent Number: 5,416,576
[45] Date of Patent: May 16, 1995

[54] SERPENTINE COIL SPECTROPHOTOMETER CELL

[75] Inventors: Theodore N. Westlake, III; Duane K. Wolcott, both of Baton Rouge, La.

[73] Assignee: The Dow Chemical Company, Midland, Mich.

[21] Appl. No.: 176,974

[22] Filed: Jan. 3, 1994

[51] Int. Cl.⁶ .............................................. G01N 21/05
[52] U.S. Cl. ..................................... 356/246; 356/440
[58] Field of Search ................. 356/246, 440; 250/343, 250/576

[56] References Cited

U.S. PATENT DOCUMENTS

| | | | |
|---|---|---|---|
| 3,679,312 | 7/1972 | Mansberg | 356/246 |
| 3,999,861 | 12/1976 | Bellinger | 356/246 |
| 4,222,670 | 9/1980 | Koshüshi | 356/440 |
| 4,841,151 | 6/1989 | Shope | 356/244 |

Primary Examiner—Richard A. Rosenberger

[57] ABSTRACT

A spectroscopic detector cell which is particularly suited to the analysis of low flowrate and small volume liquid samples in micro-flow injection analysis or titration and microbore, high pressure liquid chromatography, wherein interference from bubbles in the flow path of the light passing through the cell is substantially eliminated by using a serpentine coil of small-bore, transparent(to the light employed for a given analysis), overlapping tubing for carrying the liquid to be analyzed at a high enough velocity to sweep away any otherwise interfering bubbles that might be formed in the liquid, and by immersing the coil in a second fluid (a gas or a liquid) which possesses the same refractive index as the tubing material and which also is transparent to the light employed for a given analysis.

11 Claims, 3 Drawing Sheets

SERPENTINE COIL SPECTROPHOTOMETER CELL

Spectroscopic detector apparatus are well known in the art, and have involved passing a fluid to be analyzed (gas or liquid) in between two opposed windows through which light is passed. With the low flowrates and small volumes of the liquids to be analyzed in flow injection analysis (especially micro-flow injection analysis (micro-FIA)), flow injection titrations or microbore, high pressure liquid chromatography, however, bubbles which are formed in the flow path of the detector cell (through outgassing, for example, due to reduced pressures on the stream from a chromatograph) are difficult or almost impossible to dislodge from any sharp edges, corners and seal interfaces in the cell or from the surfaces of the windows themselves. These bubbles can interfere to a significant extent with the analysis of the liquid in question. Further, because the windows and other cell components are exposed directly to the liquid to be analyzed and to the temperatures and pressures to which the liquid is subject, a number of constraints can be placed on the construction of the detector cell and of its components which may limit the utility or effectiveness of the cell.

An exemplary spectroscopic detector cell 10 and associated monochromator 12 and photomultiplier-type detector 14 of the prior art are shown in FIG. 1, wherein a fluid to be analyzed (for example in microbore, high pressure liquid chromatography) is passed by conventional fluid connections into and from a cylindrical chamber 16 (as suggested by the flow arrows 18 and 20, respectively, provided in FIG. 1) having threaded end caps 22 at its ends, the end caps 22 forming a seal with the chamber 16 through a gasket- or O ring-type seal 24 and defining usually slotted openings therein in or over which a window material 26 is disposed. The window material is conventionally selected to transmit monochromatic light of a selected wavelength or range of wavelengths from the monochromator 12. For ultraviolet or visible light detection, quartz or sapphire is normally favored, for near infrared detection sapphire is typically employed and for infrared detection polished salt crystals may be used.

The present invention provides a novel and improved spectroscopic detector cell which is particularly suited to the analysis of low flowrate and small volume liquid samples in micro-flow injection analysis or titration and microbore, high pressure liquid chromatography, wherein interference from bubbles in the flow path of the light passing through the cell is substantially eliminated. This is accomplished in the spectroscopic cell of the present invention by using a serpentine coil of smallbore, transparent (to the light employed for a given analysis) tubing for carrying the liquid to be analyzed through the cell, and by immersing the coil in a second fluid (a gas or a liquid) which possesses the same refractive index as the tubing material and which also is transparent to the light employed for a given analysis. By causing the serpentine coil to overlap or cross itself a number of times in the volume of the cell defined between the windows (when viewed through the window receiving light from a monochromator 12 and toward the opposed window wherein light is transmitted to an associated photomultiplier-type detector 14), a sufficient quantity of the fluid may be placed in the flow path of the light for an effective analysis thereof, while at the same achieving a high enough velocity of liquid flow through the tubing to sweep away any otherwise interfering bubbles that might be formed in the liquid (for example, by outgassing in a high pressure liquid chromatography application).

FIG. 1, as already indicated above, depict a conventional monochromator, spectroscopic detector cell and detector in combination.

Figure 1:
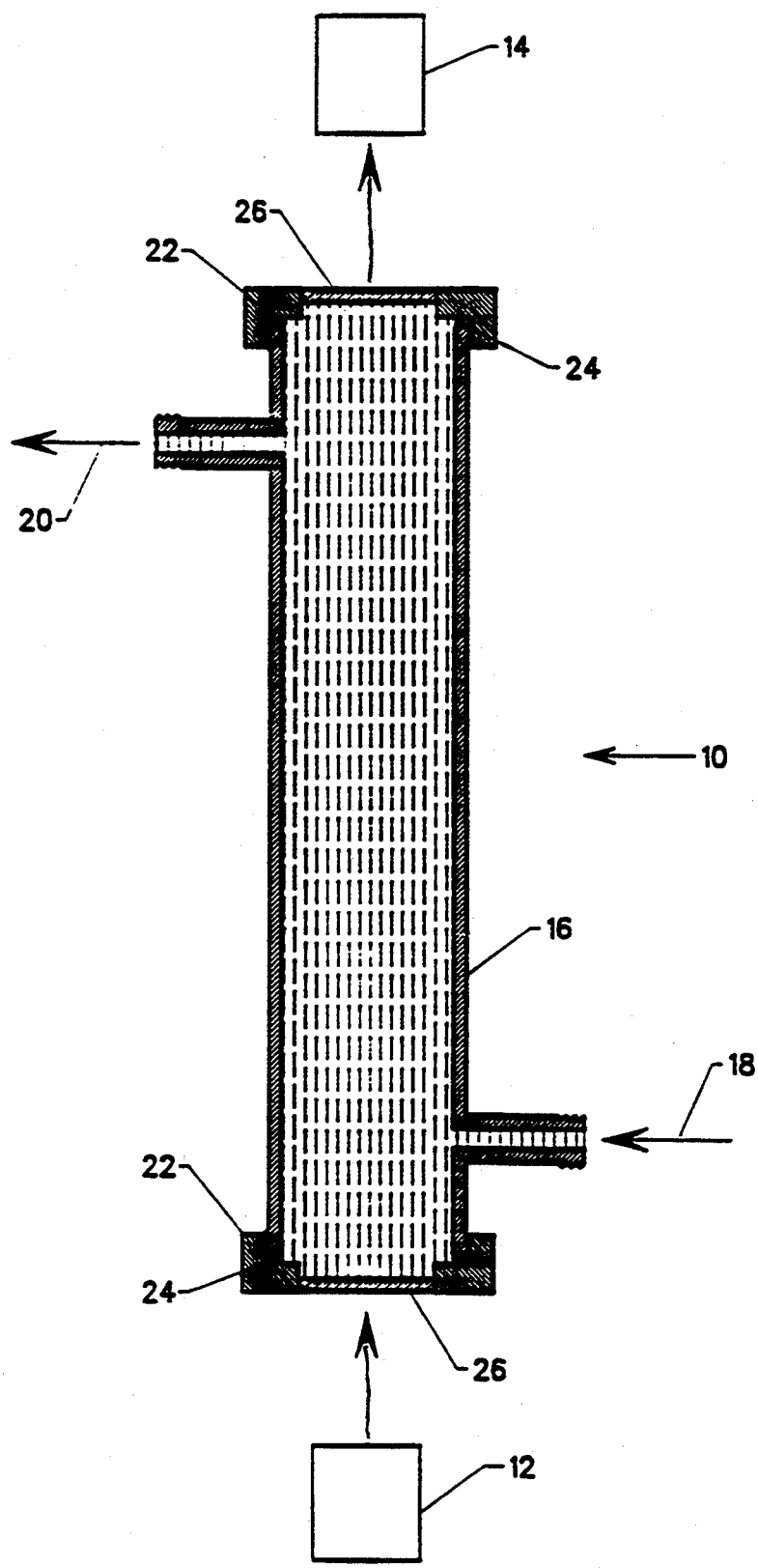
Figure 2:
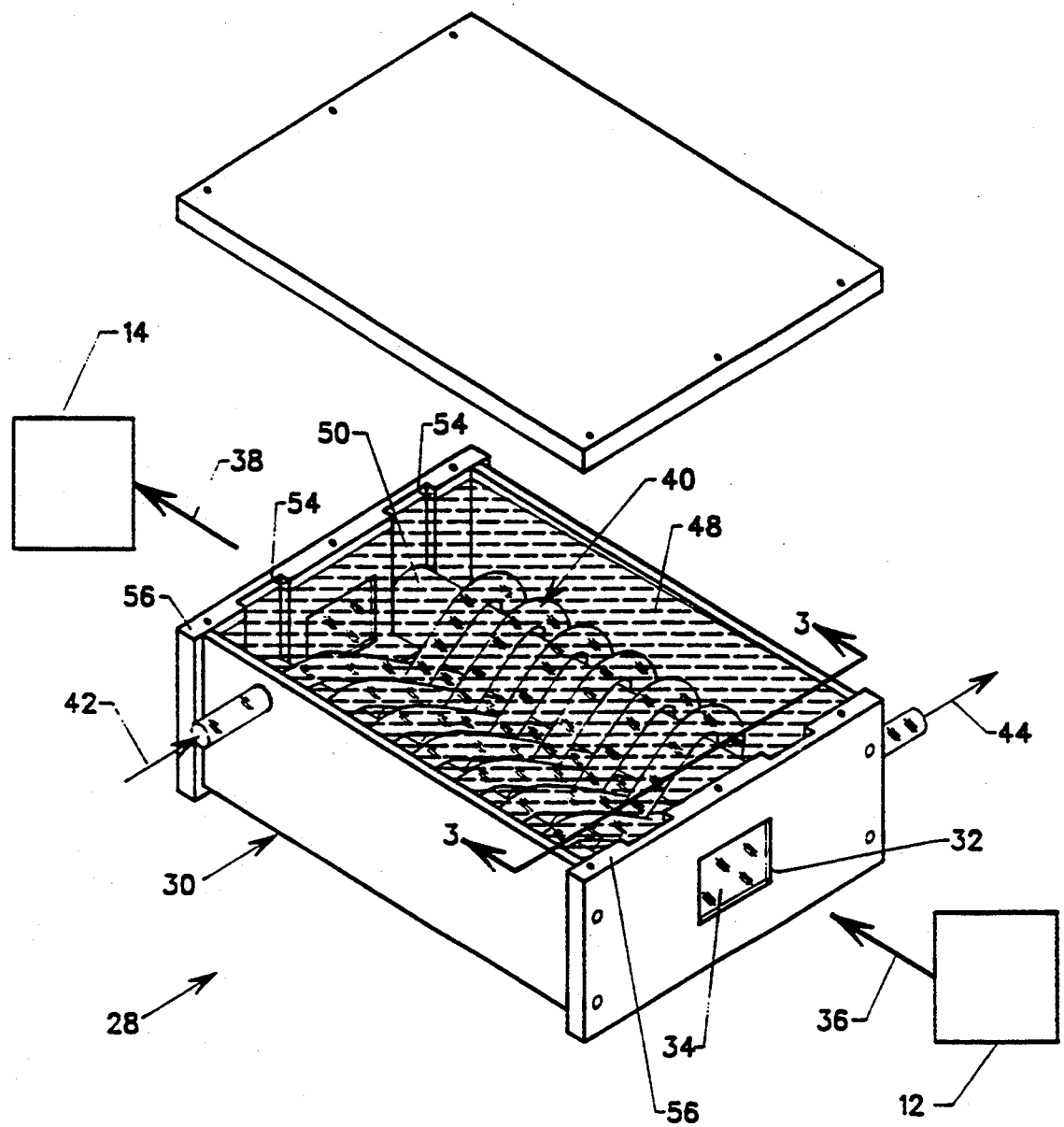
FIG. 2 illustrates a preferred embodiment of the spectroscopic detector cell of the present invention, in association with a conventional monochromator and photomultiplier-type detector.
Figure 3:
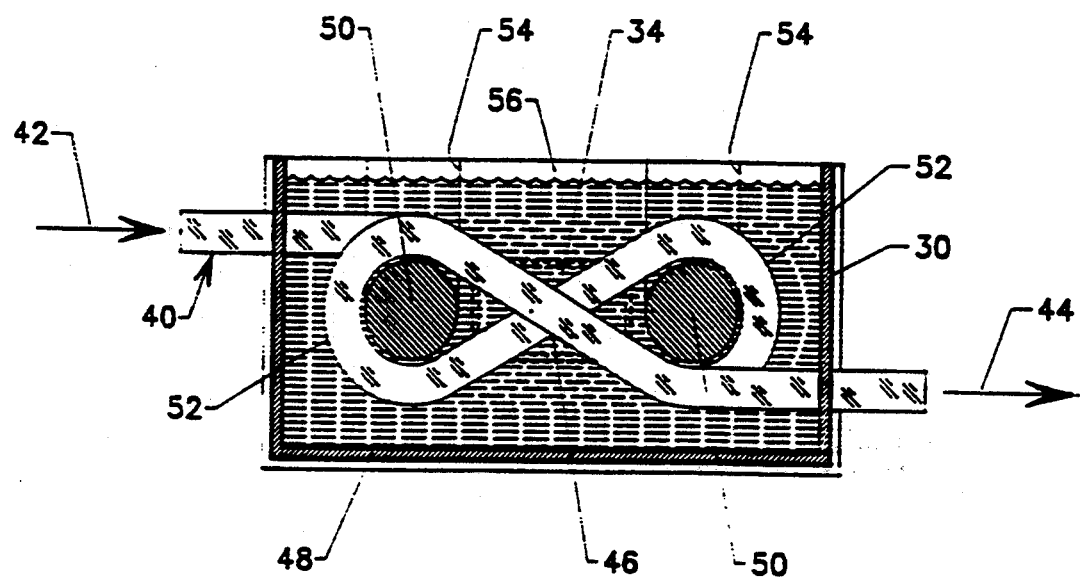
FIG. 3 is a cross-sectional view of the spectroscopic detector cell of FIG. 2, taken along line 3—3 in FIG. 2.

Referring now to the drawings, and more particularly to FIGS. 2 and 3, a preferred embodiment 28 of the spectroscopic cell of the present invention is illustrated in conjunction with a monochromator 12 and a photomultiplier-type detector 14. The cell 28 comprises a chamber 30 which defines opposed openings 32, with windows 34 being disposed in or over such openings 32 which are selected to transmit light of a selected wavelength or wavelengths from monochromator 12 and to detector 14 (such light being suggested by arrows 36 and 38, respectively).

A serpentine coil 40 of small-bore tubing is provided for carrying a flow of a liquid sample to be analyzed into and from the chamber 30 (as suggested by flow arrows 42 and 44, respectively), the form of the coil 40 suggesting a series of successive "figure eights" whose central intersections 46 (see FIG. 3) are generally aligned along a common axis. This common axis preferably coincides in the cell 28 with a line drawn from the center of one window 34 to the center of the opposed window 34 and with the flow path of light through the chamber 30 according to flow arrows 36 and 38 (see FIG. 3).

The small-bore tubing is constructed of a material which is transparent to the light employed for a given analysis, and to avoid dispersion of the light from the monochromator 12 caused by the curvature of the tubing of coil 40, the coil 40 is immersed in a fluid 48 (a gas or a liquid) which possesses the same refractive index as the tubing material, which is transparent to the light employed for a given analysis and which is compatible (in the sense of not interfering with the proper operation of the apparatus) with the materials of the cell 28, the windows 34 and any sealing materials used in the assembly of the cell 28 (not shown). In ultraviolet light or visible light detection, the coil 40 can be constructed for example of quartz-silica tubing blown in the illustrated serpentine configuration. Support rods 50 are inserted through each of the "loops" 52 of the successive figure eights of tubing which make up the coil 40, and being outside of the light path through the cell 28 (as seen in FIG. 3) can be constructed of any material which can support the coil 40 in position and which again is compatible with the fluid 48 in chamber 30.

The support rods 50 in turn are supported in grooves 54 in the chamber walls 56 on either side of the slotted openings 32 and windows 34, or more generally can be supported in any manner which permits their removal and independent insertion through the loops 52 of tubing where a substantially rigid, preformed coil 40 is employed (an earlier-mentioned example being a blown, serpentine quartz-silica coil 40). Where the coil 40 is constructed of a sufficiently flexible material, it is also possible to have the support rods 50 permanently joined (by any conventional means, including solvent welding or being integrally formed with the walls 56) to the chamber walls 56 on either side of the openings 32 and windows 34, and to weave the coil 40 through and around the rods 50 in the illustrated configuration. Those skilled in the art will appreciate further that numerous other constructions can be employed to suitably support the coil 40 in chamber 30, so long as these other constructions do not obstruct or interfere with the transmission of light through the chamber 30 between the windows 34.

The tubing which comprises the coil 40 is selected so that it is appropriate to the pressure of the liquid sample to be analyzed, and is compatible with the liquid sample. The support rods 50 and other elements of chamber 30 (and most notably the windows 34) are not in direct contact with the liquid sample and thus need not be adapted to withstand the pressures associated therewith or be compatible with the liquid sample, but need only be compatible with the refractive index fluid 48 under prevailing conditions of temperature and pressure (generally, ambient conditions).

The monochromator 12 and photomultiplier-type detector 14 are conventional elements in the art, and need not be described further. The same can be said of the various applications and possible uses of the cell 28.

Those skilled in the art will appreciate from the foregoing description that various other embodiments and constructions of the novel and improved spectrophotometer cell of the present invention are possible, which nevertheless are within the scope and spirit of the present invention in employing small-bore tubing to minimize interference from bubbles in a liquid sample to be analyzed, while placing enough of the tubing and of the liquid passing therethrough in the light path of a spectrophotometer apparatus to perform an analysis on the liquid sample. Thus it should be possible to employ other configurations of small-bore tubing in the coil 40, or to employ other constructions of the surrounding chamber 30, support rods 50, openings 32 and windows 34 to support and place the coil 40 in the illustrated configuration or some other configuration.

What is claimed is:

1. A spectrophotometer apparatus for the spectroscopic analysis of a liquid sample, comprising:
    a monochromator;
    a spectroscopic detector cell; and
    a photomultiplier-type spectroscopic detector in combination, wherein the spectroscopic detector cell includes:
        a chamber defining opposed openings;
        windows disposed in or over said opposed openings for transmitting light of a selected wavelength or range of wavelengths received from the monochromator therethrough to the photomultiplier-type detector;
        a coil of transparent tubing for carrying the liquid sample through the chamber and which overlaps itself a plurality of times in the flow path of transmitted light between the opposed windows so as to place a sufficient quantity of the liquid sample in such flow path for an effective spectroscopic analysis to be carried out on the liquid sample by the detector; and
        a second fluid disposed within the chamber and surrounding the coil of transparent tubing, which under the conditions of analysis of a given liquid sample is of the same refractive index as the material forming the transparent tubing, which also is transparent to the wavelength or range of wavelengths selected for the analysis of said liquid sample, and which is compatible with the materials forming the transparent tubing, the chamber and any sealing materials involved in containing the second fluid within the chamber and with which the second fluid has contact.

2. A spectrophotometer apparatus as defined in claim 1, wherein the coil of transparent tubing is in the form of a series of successive figure eights whose central intersections lie generally along a common axis defined between the centers of the opposed windows.

3. A spectrophotometer apparatus as defined in claim 2, wherein the spectroscopic detector cell further comprises removable support members which pass through the two loops of the successive figure eights of the coil for supporting the coil in the chamber, and for holding the central intersections of the coil in position along the common axis defined between the centers of the opposed windows.

4. A spectroscopic detector cell for the spectroscopic analysis of a liquid sample, comprising:
    a chamber defining opposed openings;
    windows disposed in or over said opposed openings for transmitting light of a selected wavelength or range of wavelengths therethrough; and
    a coil of transparent tubing for carrying the liquid sample through the chamber and which overlaps itself a plurality of times in the flow path of transmitted light between the windows so as to place a sufficient quantity of the liquid sample in such flow path for an effective spectroscopic analysis to be carried out on the liquid sample by the detector.

5. A spectroscopic detector cell as defined in claim 4, further comprising a second fluid disposed within the chamber and surrounding the coil of transparent tubing, which under the conditions of analysis of a given liquid sample is of the same refractive index as the material forming the transparent tubing, which also is transparent to the wavelength or range of wavelengths selected for the analysis of said liquid sample, and which is compatible with the materials forming the transparent tubing, the chamber and any sealing materials involved in containing the second fluid within the chamber and with which the second fluid has contact.

6. A spectroscopic detector cell as defined in claim 5, wherein the coil possesses a substantially rigid, preformed construction.

7. A spectroscopic detector cell as defined in claim 6, wherein the coil of transparent tubing is in the form of a series of successive figure eights whose central intersections lie generally along a common axis defined between the centers of the opposed windows.

8. A spectroscopic detector cell as defined in claim 7, wherein the cell further comprises removable support members which pass through the two loops of the successive figure eights of the coil for supporting the coil in the chamber, and for holding the central intersections of the coil in position along the common axis defined between the centers of the opposed windows.

9. A spectroscopic detector cell as defined in claim 4, wherein the coil possesses a substantially rigid, preformed construction.

10. A spectroscopic detector cell as defined in claim 9, wherein the coil of transparent tubing is in the form of a series of successive figure eights whose central intersections lie generally along a common axis defined between the centers of the opposed windows.

11. A spectroscopic detector cell as defined in claim 10, wherein the cell further comprises removable support members which pass through the two loops of the successive figure eights of the coil for supporting the coil in the chamber, and for holding the central intersections of the coil in position along the common axis defined between the centers of the opposed windows.

* * * * *